United States Patent [19]

Sorensen et al.

[11] Patent Number: 5,144,084

[45] Date of Patent: Sep. 1, 1992

[54] PROCESS FOR THE CONVERSION OF OLEFINS TO ALCOHOLS AND/OR ETHERS

[75] Inventors: Charles M. Sorensen, Wilmington, Del.; Philip Varghese, Voorhees; David O. Marler, Deptford, both of N.J.

[73] Assignee: Mobil Oil Corporation, Fairfax, Va.

[21] Appl. No.: 798,017

[22] Filed: Nov. 20, 1991

Related U.S. Application Data

[63] Continuation of Ser. No. 534,329, Jun. 4, 1990, abandoned, which is a continuation of Ser. No. 296,110, Jan. 12, 1989, abandoned.

[51] Int. Cl.$^5$ ............................................. C07C 41/05
[52] U.S. Cl. .................................. 568/695; 568/697; 568/897; 568/694
[58] Field of Search ................ 568/694, 695, 697, 897

[56] References Cited

U.S. PATENT DOCUMENTS

| | | |
|---|---|---|
| 2,162,913 | 6/1939 | Eversole et al. . |
| 2,477,380 | 7/1949 | Kreps et al. . |
| 2,797,247 | 6/1957 | Keith . |
| 2,798,097 | 7/1957 | Hettinger, Jr. et al. . |
| 2,805,260 | 9/1957 | Keith . |
| 2,830,090 | 4/1958 | Teter et al. . |
| 2,861,045 | 11/1958 | Lauger et al. . |
| 2,891,999 | 6/1959 | Langer, Jr. . |
| 3,006,970 | 10/1961 | Beuther et al. . |
| 3,198,752 | 8/1965 | Bridger et al. . |
| 3,810,849 | 5/1974 | Massle . |
| 3,989,762 | 11/1976 | Ester . |
| 4,042,633 | 8/1977 | Woods . |
| 4,175,210 | 11/1979 | Selwitz et al. . |
| 4,182,914 | 1/1980 | Imaizumi . |
| 4,214,107 | 7/1980 | Chang et al. . |
| 4,334,890 | 6/1982 | Kochar et al. . |
| 4,418,219 | 11/1983 | Hanes et al. . |
| 4,439,409 | 3/1984 | Puppe et al. . |
| 4,499,313 | 2/1985 | Okumura et al. . |
| 4,605,787 | 8/1986 | Chu et al. . |
| 4,714,787 | 12/1987 | Bell et al. . |
| 4,783,555 | 11/1988 | Atkins . |
| 4,827,046 | 5/1989 | Harandi .............................. 568/697 |

FOREIGN PATENT DOCUMENTS 0055045 4/1981 European Pat. Off. .

Primary Examiner—Howard T. Mars
Attorney, Agent, or Firm—Alexander J. McKillop; Charles J. Speciale; Malcolm D. Keen

[57] ABSTRACT

Olefins are converted to alcohols and/or ethers employing, as catalyst, an acidic zeolite which has been bound with an essentially non-acidic refractory oxide of at least one metal of Group IVA and/or IVB of the Period Table of the Elements, e.g., silica, titania, zirconia and/or germania.

7 Claims, No Drawings

PROCESS FOR THE CONVERSION OF OLEFINS TO ALCOHOLS AND/OR ETHERS

This is a continuation of copending application Ser. No. 07/534,329 filed on Jun. 4, 1990, which is a continuation of application Ser. No. 07/296,110 filed Jan. 12, 1989, both now abandoned.

CROSS REFERENCE TO RELATED APPLICATIONS

This application is related by subject matter to commonly assigned, copending U.S. patent application Ser. Nos. 139,543; 139,557; 139,566; 139,567; and, 139,570, each filed Dec. 30, 1987. The contents of these applications, which are concerned with the production of alcohol(s) and/or ether(s), are incorporated by reference herein.

BACKGROUND OF THE INVENTION

This invention relates to a process for the catalytic conversion of olefins to provide alcohols, ethers and their mixtures. More particularly, the invention relates to a process for the reaction of light olefins such as ethylene, propylene, butenes, pentenes, hexenes, heptenes, etc., and their mixtures, with water and/or lower alcohols to provide alcohol(s), ether(s) or mixtures thereof employing the acidic forms of certain synthetic porous crystalline materials, or zeolites, as catalysts. The alcohols, ethers and their mixtures are useful, inter alia, as high octane blending stocks for gasoline.

There is a need for an efficient catalytic process to manufacture alcohols and ethers from light olefins thereby augmenting the supply of high octane blending stocks for gasoline. Lower molecular weight alcohols and ethers such as isopropyl alcohol (IPA) and diisopropyl ether (DIPE) are in the gasoline boiling range and are known to have a high blending octane number. In addition, by-product propylene from which IPA and DIPE can be made is usually available in a fuels refinery. The petrochemicals industry also produces mixtures of light olefin streams in the $C_2$ to $C_7$ molecular weight range and the conversion of such streams or fractions thereof to alcohols and/or ethers can also provide products useful as solvents and as blending stocks for gasoline.

The catalytic hydration of olefins to provide alcohols and/or ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; and, 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., ZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of from 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature.

U.S. Pat. No. 4,783,555 describes an olefin hydration process employing a medium pore zeolite as hydration catalyst. Specific catalysts mentioned are Theta-1, said to be preferred, ferrierite, ZSM-22, ZSM-23 and NU-10.

Japanese Laid-Open Patent Application No. 60-246335 discloses the hydration of branched olefins to alcohols in the presence of a zeolite having a silica to alumina ratio of above 10.

The catalyzed reaction of olefins with alcohols to provide ethers is another well known type of process.

As disclosed in U.S. Pat. No. 4,042,633, diisopropyl ether (DIPE) is prepared from isopropyl alcohol (IPA) employing montmorillonite clay catalysts, optionally in the presence of added propylene.

U.S. Pat. No. 4,182,914 discloses the production of DIPE from IPA and propylene in a series of operations employing a strongly acidic cation exchange resin as catalyst.

In U.S. Pat. No. 4,334,890, a mixed $C_4$ stream containing isobutylene is reacted with aqueous ethanol to form a mixture of ethyl tertiary butyl ether (ETBE) and tertiary butyl alcohol (TBA).

U.S. Pat. No. 4,418,219 discloses a process for preparing methyl tertiary butyl ether (MTBE) by reacting isobutylene and methanol in the presence of boron phosphate, blue tungsten oxide or a crystalline aluminosilicate zeolite having a silica to alumina mole ratio of at least 12:1 and a Constraint Index of from 1 to about 12 as catalyst.

As disclosed in U.S. Pat. No. 4,605,787, alkyl tertalkyl ethers such as MTBE and tertiary amyl methyl ether (TAME) are prepared by the reaction of a primary alcohol with an olefin having a double bond on a tertiary carbon atom employing as catalyst an acidic zeolite having a Constraint Index of from about 1 to 12, e.g., ZSM-5, ZSM-11, ZSM-12, ZSM-23 dealuminized zeolite Y and rare earth-exchanged zeolite Y.

U.S. Pat. No. 4,714,787 discloses the preparation of ethers by the catalytic reaction of linear monoolefins with primary or secondary alcohols employing, as catalyst, a zeolite having a pore size greater than 5 Angstroms, e.g., ZSM-5, zeolite Beta, zeolite X, zeolite Y, etc. Specifically, in connection with the reaction of propylene with methanol to provide methyl isoopropyl ether (MIPE), effluent from the reactor is separated into a MIPE fraction, useful as a gasoline blending component, with unreacted propylene, methanol, by-product dimethyl ether (DME) and water at up to one mole per mole of by-product DME, either individually or in combination, being recycled to the reactor.

In European Patent Application 55,045, an olefin is reacted with an alcohol to provide an ether, e.g., isobutene and methanol are reacted to provide MTBE, in the presence of an acidic zeolite such as zeolite Beta, ZSM-5, ZSM-8, ZSM-11, ZSM-12, ZSM-23, ZSM-35, ZSM-43 and ZSM-48, and others, as catalysts.

German Patent No. 133,661 describes the reaction of isobutene and methanol to provide a mixture of products including MTBE, butanol and isobutene dimer employing acidic zeolite Y as catalyst.

Japanese Laid-open Patent Application No. 59-25345 describes the reaction of a primary alcohol with a tertiary olefin in the presence of a zeolite having a silica to alumina mole ratio of at least 10 and the X-ray diffraction disclosed therein to provide a tertiary ether.

It is a common practice in zeolite catalyst manufacture to extrude the active zeolite component with an inorganic oxide binder component such as alumina. The binder serves as a matrix for the zeolite and facilitates the extrusion process resulting in a composite product possessing good mechanical strength. In many cases, the binder component contributes little to the observed catalytic activity and can be regarded as an inert diluent for the catalytically active zeolite component. However, it has now been discovered that the activity and selectivity of zeolite catalysts used in olefin hydration/etherification may be significantly influenced by the nature of the binders with which the zeolites are composited.

SUMMARY OF THE INVENTION

It is an object of this invention to provide an efficient process for the catalytic conversion of economical, readily available sources of light olefins to alcohol(s), ether(s) or mixtures thereof which are useful, among other applications, as high octane blending stocks for gasoline.

It is another object of the invention to provide a process for catalytically converting olefin(s) to alcohol(s and/or ether(s) employing an acidic zeolite catalyst which is bound, or composited, with at least one essentially non-acidic refractory oxide of a metal of Group IVA and/or IVB of the Periodic Table of the Elements.

By way of realizing the foregoing and other objects of the invention, in a process for the conversion of at least one light olefin to at least one alcohol, ether or mixture of alcohol and ether in which the light olefin undergoes reaction with water and/or alcohol in a reaction zone in which there is present an acidic zeolite which is effective for the catalysis of said conversion, an improvement is provided which comprises employing said zeolite which has been bound with at least one essentially non-acidic refractory oxide of a metal of Group IVA and/or IVB of the Period Table of the Elements.

The alcohol(s) and/or ether(s) resulting from the foregoing improved olefin conversion process are advantageously employed as blending components for gasoline, as cosolvents for methanol to be incorporated into gasoline and for many other applications.

DESCRIPTION OF THE PREFERRED EMBODIMENTS

The present invention is applicable to the conversion of individual light olefins and mixtures of olefins of various structures, preferably within the $C_{2-7}$ range. Accordingly, the invention is applicable to the conversion of ethylene, propylene, butenes, pentenes, hexenes, heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, a typical FCC light olefin stream possesses the following composition:

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentanes | 0.7 | 0.4 |

The process of the invention is especially applicable to the conversion of propylene and propylene-containing streams to mixtures of IPA and DIPE.

When olefin is reacted with water to provide an alcohol, the reaction can be regarded as one of hydration although, of course, some product alcohol can, and does, react with olefin feed to co-produce ether. When olefin is reacted solely with alcohol to provide an ether, the reaction can be regarded as one of etherification. When olefin is reacted with both water and alcohol to provide a mixture of alcohol and ether, the resulting conversion involves both hydration and etherification reactions. In addition, other reactions such as the chemical dehydration of alcohol to ether may occur to some extent.

Lower alcohols which are suitable for reaction with light olefin herein, optionally together with water, include alcohols having from 1 to 6 carbon atoms, i.e., methanol, ethanol, propanol, isopropyl alcohol, n-butanol, tert-butanol, the pentanols and the hexanols.

The operating conditions of the improved olefin conversion process herein are not especially critical. They include a temperature ranging from ambient up to about 300° C., preferably from about 50° to about 220° C. and more preferably from about 100° to about 200° C., a total system pressure of at least about 5 atm, preferably at least about 20 atm and more preferably at least about 40 atm, a total water and/or alcohol to olefin mole ratio of from about 0.1 to about 30, preferably from about 0.2 to about 15 and most preferably from about 0.3 to about 5. When the conversion is primarily one of hydration, it may be preferable to operate at low water to total olefin mole ratios as disclosed in commonly assigned copending U.S. patent application Ser. No. 139,567 referred to above, e.g., at water to total olefin mole ratios of less than about 1. Those skilled in the art will recognize that selection of specific operating conditions for a particular feed will influence product distribution.

It will also be appreciated that the precise conditions selected should, to some extent, reflect the nature of the olefin feed. For example, isoolefins generally require milder process conditions than straight chain olefins. Thus, in the case of isobutylene, $CH_2=CH(CH_3)_2$, good conversions to ether can be obtained with process conditions of from about 30° C. to about 100° C., a pressure which is at least sufficient to maintain the isobutylene in the liquid phase, e.g., about 3 atm or higher, a water and/or alcohol to isobutylene mole ratio of from about 0.1 to about 30, preferably from 0.2 to about 15 and most preferably from about 0.3 to about 5 and an LHSV of from about 0.1 to about 25.

The olefin conversion process of this invention can be carried out under liquid phase, vapor phase or mixed vapor-liquid phase conditions in batch or in a continuous manner using a stirred tank reactor or fixed bed flow reactor, e.g., of the trickle-bed, liquid-up-flow, liquid-down-flow, counter-current, co-current, etc., type. Reaction times of from about 20 minutes to about 20 hours when operating in batch and an LHSV of from about 0.1 to about 25 when operating continuously are generally suitable It may, of course, be advantageous to recover any unreacted olefin and recycle it to the reactor.

When seeking to maximize the production of ether by the hydration of olefin, the aqueous product effluent from the olefin hydration reactor containing alcohol and ether can be introduced into a separator, e.g., a distillation column, for recovery of ether. The dilute aqueous solution of alcohol may be then introduced into a second separator, e.g., another distillation column, where a water/alcohol azeotrope is recovered. A fraction of the azeotrope may be fed into a dehydration reactor of conventional or otherwise known type and operation to provide a further quantity of ether which can be combined with the ether previously recovered from the olefin hydration reactor. By blending various product streams, almost any ratio of alcohol/ether can be obtained. When alcohol/ether mixtures are to be used as gasoline blending stocks, this capability for adjusting the ratios of alcohol to ether offer great flexibility in meeting the octane requirements for given gasoline compositions. Regulatory considerations aside, alcohol/ether mixtures, e.g., IPA/DIPE mixtures, can constitute up to about 20 weight percent or so of the gasoline to which they are added.

A particularly advantageous procedure for producing mixtures of alcohol and ether, and in particular IPA and DIPE, from the hydration of an olefin-containing feed (a propylene-containing feed in the case of IPA/DIPE mixtures) employing a large pore zeolite such as zeolite Y or zeolite Beta is described in U.S. patent application Ser. No. 139,543 referred to above. In accordance with this procedure as applied, e.g., to the production of IPA/DIPE mixtures, a fresh propane/propylene-containing feed (readily available in many petroleum refineries) and fresh water are cofed, together with recycled unreacted propylene and recycled water from a decanter, into a hydration reactor. The reactor effluent is passed to a separator unit with propane and unconverted propylene being recycled to the reactor, part of the gaseous mixture being purged in order to avoid build-up of propane in the recycle loop. The liquid products from the separator unit are introduced into a distillation unit where an azeotropic mixture of IPA, DIPE, water and propylene oligomers (mostly $C_6$ olefin) is distilled off and, following cooling, is introduced into a decanter in which phase separation takes place. The upper layer contains mostly DIPE, e.g., 90 weight percent or more, and relatively little water, e.g., 1 weight percent or so. The lower layer is largely water containing negligible quantities of IPA and DIPE. The quantity of the decanter overheads which is recycled can be regulated so as to control the water content in the final product. The bottom fraction of the distillation unit, mainly IPA, is combined with DIPE in the decanter overheads to provide the final IPA/DIPE mixture.

Where it is desired to separate out the alcohol from an alcohol/ether mixture and thus provide essentially pure ether, one can advantageously practice the procedure of U.S. patent application Ser. No. 139,566 referred to above. According to this process as applied to the production of DIPE, the propylene component of a mixed propane/propylene feed undergoes hydration in the presence of a large pore zeolite olefin hydration catalyst, e.g., zeolite Y or zeolite Beta, in a hydration reactor with the effluent therefrom being passed to a separator operating below the olefin hydration reaction temperature. There, two liquid phases form, the aqueous phase being removed and recycled to the hydration reactor. The hydrocarbon-rich phase is flashed to a lower pressure to effect separation of the unreacted $C_3$ components. The flashed product, now containing a substantial amount of IPA product, is introduced to a distillation unit operated at or below atmospheric pressure to effect further purification of the DIPE. The azeotropic IPA, DIPE and water overhead product containing a small amount of propylene oligomer is condensed and thereafter contacted with reactor feed water. The resulting phase separation provides a DIPE product containing at most negligible amounts of IPA and water, e.g., 1.0 weight percent and 0.5 weight percent of these materials, respectively. The remaining aqueous phase can be recycled to the reactor.

The catalyst employed in the olefin conversion process of this invention can be any zeolite which is effective for the catalysis of the reaction of olefin(s) with water and/or alcohol(s) to produce alcohol(s), ether(s) or their mixtures. Useful zeolite catalysts include those disclosed in the prior art discussed above as well as in pending U.S. patent application Ser. Nos. 139,557, 139,567 and 139,570 referred to above.

The term "zeolite" as used herein is meant to include the class of porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst.

Representative of the zeolites which are useful herein are zeolite Beta, zeolite X, zeolite L, zeolite Y, ultrastable zeolite Y (USY), dealuminized Y (Deal Y), mordenite, ZSM-3, ZSM-5, ZSM-12, ZSM-20, ZSM-23, ZSM-35, ZSM-38, ZSM-50, MCM-22 and mixtures of any of the foregoing.

Also included within the definition of the useful zeolites are crystalline porous silicoaluminophosphates such as those disclosed in U.S. Pat. No. 4,440,871, the catalytic behavior of which is similar to that of the aluminosilicate zeolites.

Zeolite Beta is described in U.S. Reissue Pat. No. 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192, 3,354,077, 3,375,065, 3,402,996, 3,449,070 and 3,595,611, to which reference is made for details of this catalyst.

Dealuminized zeolite Y can be prepared by the method disclosed in U.S. Pat. No. 3,442,795, to which reference is made for details of this catalyst.

Zeolite ZSM-3 is described in U.S. Pat. No. 3,415,736, to which reference is made for details of this catalyst.

Zeolite ZSM-5 is described in U.S. Pat. No. Re. 29,948 (of original U.S. Pat. No. 3,702,886), to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-23 is described in U.S. Pat. No. 4,076,842, to which reference is made for the details of this catalyst.

Zeolite ZSM-35 is described in U.S. Pat. No. 4,016,245, to which reference is made for the details of this catalyst.

Zeolite ZSM-38 is described in U.S. Pat. No. 4,046,859, to which reference is made for the details of this catalyst.

Zeolite ZSM-50 is described in U.S. Pat. No. 4,640,829, to which reference is made for details of this catalyst.

Zeolite MCM-22 and the use of this zeolite to catalyze the reaction of olefin(s) with water to provide alcohol(s), ether(s) or mixtures thereof is disclosed in U.S. patent application Ser. No. 139,557 referred to above.

Zeolite MCM-22, or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area (greater than 400 m²/gm as measured by the BET [Bruenauer, Emmet and Teller] test) and unusually large sorption capacity when compared to previously described crystal structures having similar X-ray diffraction patterns. As is evident from the above formula, MCM-22 is synthesized nearly free of Na cations It can, therefore, be used as an olefin hydration/etherification catalyst with acid activity without an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for olefin hydration/etherification. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern which is distinguished from the patterns of other known crystalline materials by the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W | more specifically by the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (A) | Relative Intensity, I/Io × 100 |
|---|---|
| 30.0 ± 2.2 | W-M |
| 22.1 ± 1.3 | W |
| 6.00 ± 0.1 | W-M |
| 4.06 ± 0.07 | W-S |
| 3.91 ± 0.07 | M-VS |

Most specifically, the calcined crystalline material has an X-ray diffraction pattern which includes the lines listed in Table IV below:

TABLE IV

| Interplanar d-Spacing (A) | Relative Intensity I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |

TABLE IV-continued

| Interplanar d-Spacing (A) | Relative Intensity I/Io × 100 |
|---|---|
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstroms Units (A), corresponding to the recorded lines, were determined. In Tables I–IV, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| YO$_2$/X$_2$O$_3$ | 10–80 | 10–60 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

In a preferred method of synthesizing zeolite MCM-22, the YO$_2$ contains a substantial amount of solid YO$_2$, e.g., at least about 30 wt. % solid YO$_2$. Where YO$_2$ is silica, the use of a silica source containing at least about 30 wt. % solid silica, e.g., Ultrasil (a precipitated, spray dried silica containing about 90 wt. % silica) or HiSil (a precipitated hydrated SiO$_2$ containing about 87 wt. % silica, about 6 wt. % free H$_2$O and about 4.5 wt. % bound H$_2$O of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine which has the following structural formula:

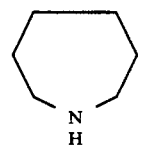

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

The zeolite olefin hydration/etherification catalysts selected for use herein will generally possess an alpha value of at least about 1. "Alpha value", or "alpha number", is a measure of zeolite acidic functionality and is more fully described together with details of its measurement in J. Catalysis, 61, pp. 390–396 (1980). Zeolites of relatively low acidity (e.g., zeolites possessing alpha values of less than about 200) can be prepared by a variety of techniques including (a) synthesizing a zeolite with a high silica/alumina ratio, (b) steaming, (c) steaming followed by dealuminization and (d) substituting framework aluminum with other trivalent metal species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

Prior to their use as olefin hydration/etherification catalysts, the as-synthesized zeolite crystals should be subjected to thermal treatment to remove part or all of any organic constituent present therein. In addition, the zeolites should be at least partially dried prior to use. This can be done by heating the crystals to a temperature in the range of from about 200° C. to about 595° C. in an inert atmosphere, such as air, nitrogen, etc. and atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite olefin hydration/etherification catalyst herein, especially in their metal, hydrogen and ammonium forms, can be beneficially converted to other forms by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The original cations associated with the zeolites utilized herein can be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to VIII of the Periodic Table including, by way of example, iron, nickel, cobalt, copper, zinc, platinum, palladium, calcium, chromium, tungsten, molybdenum, rare earth metals, etc. These metals can also be present in the form of their oxides.

A typical ion-exchange technique involves contacting a particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251 and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

The binder material herein can be selected from among any of the essentially non-acidic refractory oxides of metals of Groups IVA and IVB of the Periodic Table of the Elements. Particularly useful are the oxides of silicon, germanium, titanium and zirconium. Combinations of such oxides with other oxides are also useful provided that at least about 40 weight percent, and preferably at least 50 weight percent, of the total oxide is one or a combination of the aforesaid Group IVA and/or Group IVB metal oxides. Thus, mixtures of oxides which can be used to provide the binder material herein include titania-alumina, titania-magnesia, titania-zirconia, titania-thoria, titania-beryllia, titania-silica-thoria, silica-alumina-zirconia, silica-alumina-magnesia and silica-titania-zirconia, zirconia-alumina, silica-zirconia, etc.

In preparing the refractory oxide-bound zeolite catalyst, it is generally advantageous to provide at least a part of the binder in colloidal form as this has been found to facilitate the extrusion of the bound zeolite which can otherwise be accomplished in accordance with known and conventional techniques. When a colloidal metal oxide binder is employed, it can represent anywhere from about 1 to about 100 weight percent of the total binder present. For example, in the case of silica, amounts of colloidal silica ranging from about 2 to about 60 weight percent of the total binder generally provide good results. The relative proportions of zeolite and refractory oxide binder on an anhydrous basis can vary widely with the zeolite content ranging from between about 1 to about 99 weight percent, and more usually in the range of from about 20 to about 80 weight percent, of the dry composite.

In the examples which follow in which all parts are by weight, Examples 1 to 3 are illustrative of the preparation of zeolites which are useful as catalysts herein and Examples 4 to 6 are illustrative of the olefin conversion process of this invention.

EXAMPLE 1

This example illustrates the preparation of zeolite MCM-22.

Sodium aluminate (43.5% $Al_2O_3$, 32.2% $Na_2O$, 25.6% $H_2O$), 12.86, was dissolved in a solution containing 12.8 g 50% NaOH solution and 1320 g $H_2O$. To this was added 57.6 g hexamethyleneimine. The resulting solution was added to 109.4 g of Ultrasil, a precipitated, spray-dried silica (about 90% $SiO_2$).

The reaction mixture had the following composition, in mole ratios:

$SiO_2/Al_2O_3 = 30.0$
$OH/SiO_2 = 0.18$
$H_2O/SiO_2 = 44.9$
$Na/SiO_2 = 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538°, the X-ray diffraction pattern contained the major lines listed in Table V. The sorption capacities of the calcined material were measured to be:

$H_2O$ (12 Torr): 15.2 wt. %
Cyclohexane (40 Torr): 14.6 wt. %
n-Hexane (40 Torr): 16.7 wt. %

The surface area of the calcined crystalline material was measured to be 494 $m^2/g$.

The chemical composition of the calcined material was determined to be as follows:

| Component | wt % |
| --- | --- |
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio - | 21.1 |

TABLE V

| Degrees 2-Theta | Interplanar d-Spacing (A) | I/I$_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

The MCM-22 crystals are combined with titania or other essentially non-acidic refractory metal oxide, e.g., 35 parts of the latter and 65 parts by zeolite, to provide an olefin hydration/etherification catalyst in accordance with the present invention.

EXAMPLE 2

This example illustrates the preparation of 35 wt % Ti/65 wt % zeolite Beta and 35 Wt % Zr/65 wt % zeolite Beta olefin hydration/etherification catalyst compositions.

48.5 Parts of 50% tertiary ammonium bromide were added to a mixture containing 5.5 parts NaOH, 5.45 parts Al$_2$(SO$_4$)$_3$.14H$_2$O, 29.5 parts HiSil 233, 1.0 parts zeolite beta seeds and 116.88 parts deionized water. The reaction mixture was then heated to 280° F. and stirred in an autoclave at that temperature for crystallization. After full crystallinity was achieved, the resulting zeolite Beta crystals were separated from the remaining liquid by filtration, washed with water and dried.

Portions of the zeolite Beta crystals were separately combined with titania and zirconia to form a mixture of 65 parts zeolite and 35 parts metal oxide binder. Enough water was added to the mixture so that the resulting catalyst could be formed into an extrudate. The catalyst was activated by calcining first in nitrogen at 1000° F. followed by aqueous exchanges with 1.0N ammonium nitrate solution and calcining in air at 1000° F.

EXAMPLE 3

This example illustrates the preparation of 35 wt % Ti/65 wt % ZSM-35 and 35 wt % Zr/65 wt % ZSM-35 olefin hydration/etherification catalyst compositions.

3.2 Parts of pyrrolidine were added to a mixture containing 1.38 parts 50% NaOH, 1.18 parts Al$_2$(SO$_4$)$_3$.14-H$_2$O, 3.2 parts HiSil 233 and 7.5 parts deionized water. The reaction mixture was then heated to 220° F. and stirred in an autoclave at that temperature for crystallization. After full crystallinity was achieved, the resulting ZSM-35 crystals were separated from the remaining liquid by filtration, washed with water and dried.

Portions of the ZSM-35 crystals were separately combined with titania and zirconia to form a mixture of 65 parts zeolite and 35 parts metal oxide binder. Enough water was added to the mixture so that the resulting catalyst could be formed into an extrudate. The catalyst was activated by calcining first in nitrogen at 1000° F., followed by aqueous exchanges with 1.0N ammonium nitrate solution and calcining in air at 1000° F.

EXAMPLE 4

This example illustrates the improved results obtained when conducting olefin hydration/etherification with non-acidic metal oxide-bound zeolite Beta olefin hydration catalysts, i.e., the titania- and zirconia-bound zeolite Beta catalyst compositions of Example 2, compared with an acidic metal oxide-bound zeolite Beta, e.g., zeolite bound with 35 parts of alumina.

The hydration conditions included the use of essentially pure propylene as the feed, a total system pressure of 1000 psig, a temperature of 330° F., a weight hourly space velocity (WHSV) based on propylene of 0.62 and a mole ratio of water to propylene of 0.5.

The results of the olefin hydration/etherification operations are set forth in Table VI as follows:

TABLE VI

Propylene Hydration/Etherification Using Various Metal Oxide-Bound Zeolite Beta Catalysts

| | Zeolite Olefin Hydration/ Etherification Catalyst | | |
| --- | --- | --- | --- |
| | Al$_2$O$_3$/Beta | TiO$_2$/Beta | ZrO$_2$/Beta |
| Propylene Conversion, % | 44.9 | 69.0 | 65.7 |
| Water Conversion, % | 53.7 | 78.4 | 75.3 |
| DIPE Selectivity, % | 57.3 | 58.9 | 61.5 |
| IPA Selectivity, % | 39.7 | 37.0 | 34.2 |
| Oligomer Selectivity | 3.0 | 4.1 | 4.3 |

As these data show, propylene conversion activity is much higher for the titania- and zirconia-bound zeolite catalysts. In addition, DIPE selectivity is also higher compared to the alumina-bound zeolite catalyst.

EXAMPLE 5

The propylene hydration/etherification operations of Example 4 were substantially repeated except that the catalysts were 35 weight percent alumina-bound ZSM-35 and 35 weight percent titania-bound ZSM-35 and the mole ratio of water to propylene was 2.

The results of the hydration reactions are set forth in Table VII as follows:

TABLE VII

Propylene Hydration Using Various Metal Oxide-Bound ZSM-35 Catalysts

| | Zeolite Olefin Hydration/ Etherification Catalyst | |
|---|---|---|
| | $Al_2O_3$/ZSM-35 | $TiO_2$/ZSM-35 |
| Propylene Conversion, % | 55.1 | 72.7 |
| Water Conversion, % | 25.3 | 37.5 |
| IPA Selectivity, % | 99.5 | 98.4 |

As these data show, the titania-bound zeolite catalyst provided much higher propylene conversion compared to the alumina-bound zeolite.

EXAMPLE 6

A zeolite Beta catalyst composition was prepared much as described in Example 2, supra, except that the binder was 17 weight parts of silica.

| | |
|---|---|
| Pressure: | 200 psig |
| Temperature: | 200° F. |
| Water:Isobutylene Mole Ratio: | 3.2 |
| Time on Stream: | 116.5 hr. |
| Weight Hourly Space Velocity (WHSV), based on isobutylene: | 4.9 |
| Liquid Hourly Space Velocity (LHSV): | 9.3 |

The feed possesses the following wt. % composition:

| | |
|---|---|
| Water: | 24.8 |
| Isopropanol: | 39.6 |
| Isobutylene: | 35.6 |

The percent conversions and product selectivities are set forth in Table VIII as follows:

TABLE VIII

| Conversion, % | Total Conversion | Water | Isopropanol | Isobutylene |
|---|---|---|---|---|
| | 42.4 | 40.0 | 3.6 | 87.3 |
| Product Selectivity | T-Butyl Alcohol | Isopropyl t-Butyl Ether | Oligomers | |
| | 90.1 | 8.2 | 1.8 | |

What is claimed is:

1. In a process for the hydration of an light olefin feed comprising propylene to iso-propyl alcohol, di-iso-propyl ether or mixtures of iso-propyl alcohol and di-iso-propyl ether in which the light olefin feed undergoes reaction with water and/or iso-propyl alcohol at a temperature from ambient up to about 300° C., a pressure of at least 5 Atm., at a mole ratio of water and/or iso-propyl alcohol to total olefin in the reaction zone from about 0.1 to about 30, in a reaction zone in which there is present an acidic zeolite hydration catalyst comprising zeolite beta, the improvement which comprises employing said zeolite which has been bound with a binder which consists essentially of at least one essentially non-acidic refractory oxide selected from the group consisting of titania and zirconia.

2. The process of claim 1 in which the olefin feed comprises ethylene and propylene.

3. The process of claim 1 in which the olefin feed comprises butylene and propylene.

4. The process of claim 1 wherein the mole ratio of water to total olefin in the reaction zone is from about 0.2 to about 15.

5. The process of claim 1 wherein the mole ratio of water to total olefin in the reaction zone is from about 0.3 to about 5.

6. The process of claim 1 in which at least a portion of the metal oxide binder is in colloidal form.

7. The process of claim 1 in which the catalyst is in the form of an extrudate.

* * * * *